US011786382B2

(12) United States Patent
Auberger et al.

(10) Patent No.: US 11,786,382 B2
(45) Date of Patent: Oct. 17, 2023

(54) JOINT DEVICE

(71) Applicant: Otto Bock Healthcare Products GmbH, Vienna (AT)

(72) Inventors: Roland Auberger, Vienna (AT); Christian Breuer-Ruesch, Vienna (AT); Sebastian Krepper, Markgrafneusiedl (AT)

(73) Assignee: Otto Bock Healthcare Products GmbH, Vienna (AT)

( * ) Notice: Subject to any disclaimer, the term of this patent is extended or adjusted under 35 U.S.C. 154(b) by 174 days.

(21) Appl. No.: 16/620,444

(22) PCT Filed: Jun. 6, 2018

(86) PCT No.: PCT/EP2018/064918
§ 371 (c)(1),
(2) Date: Dec. 6, 2019

(87) PCT Pub. No.: WO2018/228892
PCT Pub. Date: Dec. 20, 2018

(65) Prior Publication Data
US 2020/0163781 A1 May 28, 2020

(30) Foreign Application Priority Data
Jun. 12, 2017 (DE) .......................... 102017112911.1

(51) Int. Cl.
*A61F 2/64* (2006.01)
*A61F 5/01* (2006.01)
(Continued)

(52) U.S. Cl.
CPC .............. *A61F 2/64* (2013.01); *A61F 5/0123* (2013.01); *A61F 2/741* (2021.08);
(Continued)

(58) Field of Classification Search
CPC ...... A61F 2005/0134; A61F 2005/0155; A61F 2005/0169
See application file for complete search history.

(56) References Cited

U.S. PATENT DOCUMENTS 4,139,750 A 2/1979 Rau
6,039,707 A 3/2000 Crawford et al.
(Continued)

FOREIGN PATENT DOCUMENTS

CN 104661620 A 5/2015
CN 204562790 U 8/2015
(Continued)

OTHER PUBLICATIONS

"International Search Report and Written Opinion of the International Searching Authority," issued in connection with Int'l Appl. No. PCT/EP2018/064918, dated Oct. 17, 2018 (16 pages).
(Continued)

*Primary Examiner* — David H Willse
(74) *Attorney, Agent, or Firm* — Holland & Hart LLP

(57) ABSTRACT

A joint device of an orthosis or prosthesis or for an orthosis or prosthesis with an upper part, a lower part, a joint that comprises a joint axis, about which the upper part is mounted such that it can be swivelled relative to the lower part, and an actuator, which is designed to influence a swivelling of the upper part relative to the lower part. The actuator is mounted at an upper part fixing point on the upper part and at a lower part fixing point on the lower part. At least two joints are arranged between the upper part fixing point and the lower part fixing point, wherein the joints enable a swivelling of the actuator relative to the upper part fixing point and the lower part fixing point, and the joints each form at least one joint axis, at least one of which is not oriented parallel to the joint axis.

18 Claims, 6 Drawing Sheets

(51) Int. Cl.
*A61F 2/70* (2006.01)
*A61F 2/74* (2006.01)
*A61F 2/50* (2006.01)
*A61F 2/68* (2006.01)

(52) U.S. Cl.
CPC ............... *A61F 2002/5006* (2013.01); *A61F 2002/5038* (2013.01); *A61F 2002/5041* (2013.01); *A61F 2002/6818* (2013.01); *A61F 2002/701* (2013.01); *A61F 2005/0134* (2013.01); *A61F 2005/0155* (2013.01); *A61F 2005/0169* (2013.01)

(56) References Cited

U.S. PATENT DOCUMENTS

| | | | |
|---|---|---|---|
| 2003/0109817 A1* | 6/2003 | Berl | A61F 5/0123 602/5 |
| 2007/0010378 A1 | 1/2007 | Katoh et al. | |
| 2009/0076618 A1 | 3/2009 | Auberger et al. | |
| 2010/0130894 A1 | 5/2010 | Ikeuchi | |
| 2011/0071452 A1 | 3/2011 | Auberger | |
| 2012/0259253 A1 | 10/2012 | Bonutti et al. | |
| 2015/0272811 A1 | 10/2015 | Choi et al. | |
| 2018/0170204 A1 | 6/2018 | Hell | |

FOREIGN PATENT DOCUMENTS

| | | | | |
|---|---|---|---|---|
| CN | 104940004 A | | 9/2015 | |
| CN | 106109175 A | | 11/2016 | |
| CN | 106602969 A | | 4/2017 | |
| DE | 1261277 B | | 2/1968 | |
| DE | 102006012716 B3 | | 1/2008 | |
| DE | 102008024748 A1 | | 12/2009 | |
| DE | 102012002552 A1 | | 8/2013 | |
| DE | 10 2012 023 023 A1 | | 5/2014 | |
| DE | 102015113799 A1 | | 2/2017 | |
| EP | 1600129 A1 | | 11/2005 | |
| EP | 2254532 B1 | | 8/2012 | |
| JP | 52-124363 A | | 10/1977 | |
| JP | 2007117645 A | | 5/2007 | |
| JP | 2014-076517 | | 5/2014 | |
| RU | 2043091 C1 | | 9/1995 | |
| RU | 2064294 C1 | | 7/1996 | |
| RU | 2089138 C1 | | 9/1997 | |
| WO | 2001021114 A1 | | 3/2001 | |
| WO | 02/10312 A1 | | 2/2002 | |
| WO | WO 2004/008987 A2 | * | 1/2004 | ............ A61F 5/0113 |
| WO | 2004/043307 A1 | | 5/2004 | |
| WO | WO 2011/067483 A2 | * | 6/2011 | ............... A61F 5/01 |
| WO | 2011123928 A1 | | 10/2011 | |
| WO | WO 2012/171000 A1 | * | 12/2012 | ............... A61F 5/00 |
| WO | 2014/019872 A1 | | 2/2014 | |

OTHER PUBLICATIONS

Japan Patent Office, "Notice of Reasons for Refusal", issued in connection with Japan Patent Application No. 2019-562277 dated Jun. 1, 2022 (9 pages).

* cited by examiner

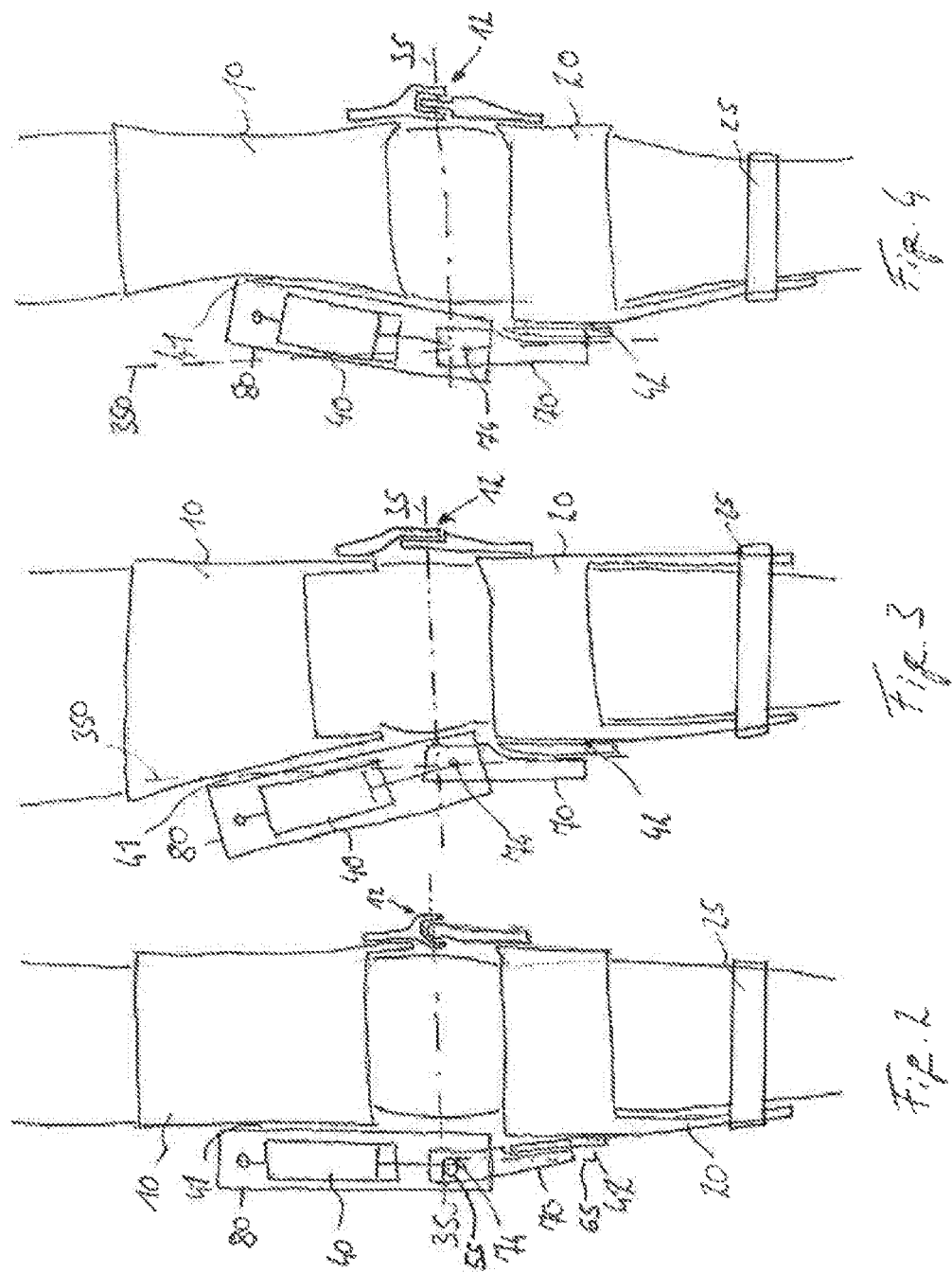

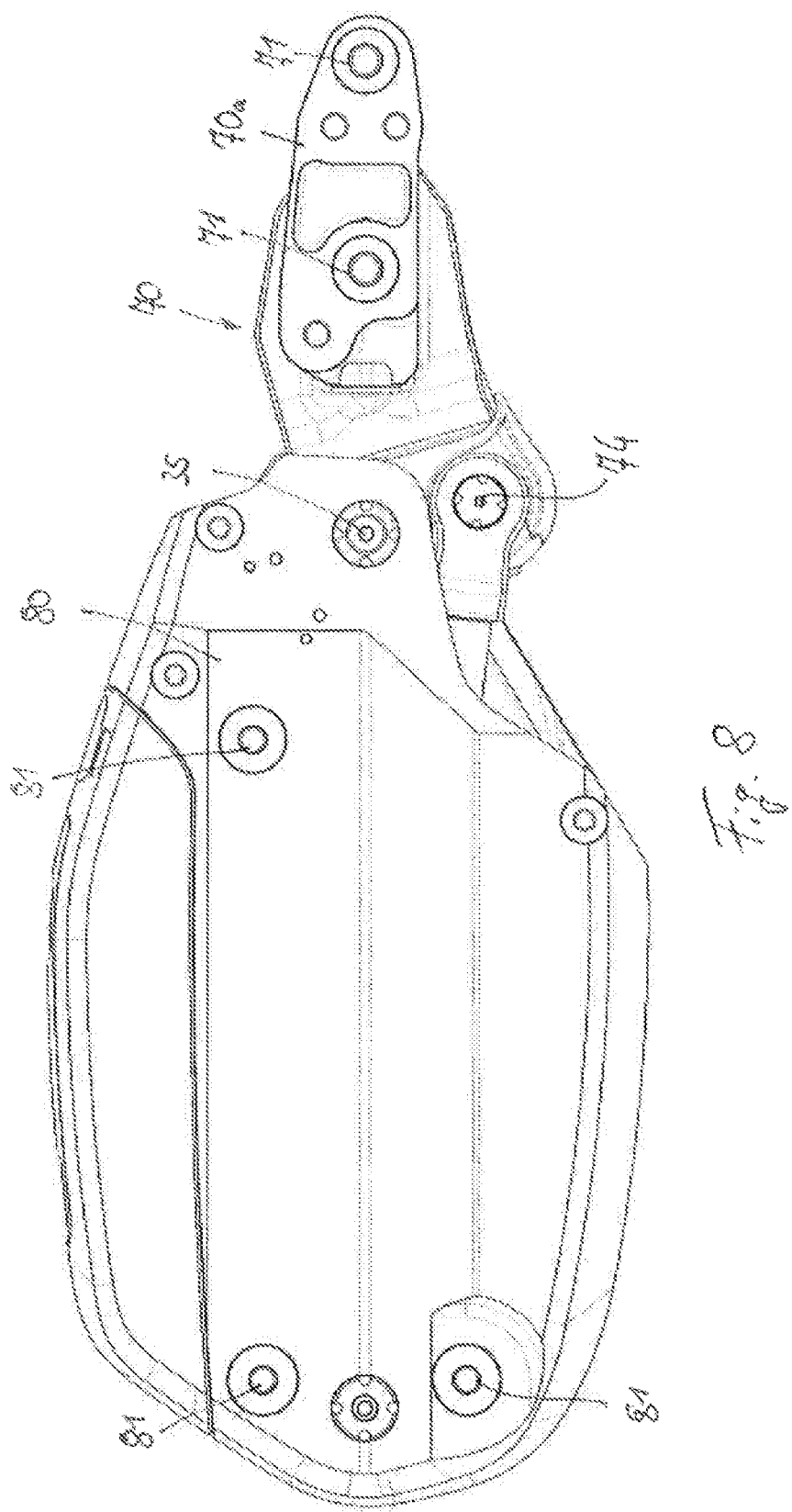

JOINT DEVICE

CROSS REFERENCE TO RELATED APPLICATIONS

This application is a U.S. National Entry and claims priority to PCT International Patent Application No. PCT/EP2018/064918, filed 6 Jun. 2018, and entitled JOINT DEVICE, which claims priority to Germany Patent Application No. 102017112911.1 filed 12 Jun. 2017, the entire disclosures of which are incorporated herein by this reference.

TECHNICAL FIELD

The invention relates to a joint device for a prosthesis or an orthosis or of a prosthesis or orthosis with an upper part, a lower part, with a joint that comprises a joint axis about which the upper part is mounted such that it can be swivelled relative to the lower part, and an actuator, which is designed to influence a swivelling of the upper part relative to the lower part, wherein the actuator is mounted at an upper part fixing point on the upper part and at a lower part fixing point on the lower part.

BACKGROUND

Joint devices can be used in orthoses or prostheses. Orthoses are used, among other things, to support or retain the function of the remaining limb. To this end, the orthosis is attached to the remaining limb. In the case of an orthosis of the lower limb, such as an orthosis that overlaps the knee joint, rails are laid on the upper leg and the lower leg, said rails being connected to one another via an orthotic knee joint. In the case of an ankle orthosis, the foot is fixed to a foot part, which is connected to a lower leg rail via an orthotic ankle joint. The same applies for a hip joint orthosis or for an orthosis that bridges more than two natural joints. Orthoses can also be used on upper limbs.

Missing limbs are replaced by prostheses. If natural joints, such as a knee joint, are missing, the missing natural knee joint is replaced by a prosthetic knee joint. The upper part of the prosthetic knee joint is attached to a lower leg stump via an upper leg socket. The lower part of the prosthetic knee joint is fixed to the upper leg part such that it can be swivelled. A lower leg tube and a prosthetic foot, where applicable with a prosthetic ankle joint, are arranged on the lower leg part.

In the case of both prostheses and orthoses, actuators may be used to influence the movements of the individual components, for instance to support or prevent a swivel movement. A movement is supported by supplying energy from an energy store, for example via a spring mechanism or via a motor drive, which is supplied with energy from an energy store for storing energy, wherein this energy is normally electrical energy. To prevent a movement, for example to dampen a flexion or extension movement or to decelerate, dampers—such as hydraulic dampers or pneumatic dampers—are used. End stop elements may be used in the respective joint direction in order to ensure a soft end stop when a maximum position is reached, be it a flexion or an extension.

A joint device for lower limbs is described, for instance, in DE 10 2015 113 799 A1.

In orthotics technology in particular, but also in the field of prosthetics, it has thus far been necessary to mount available components parallel to preserved body parts, so that swivel axes align with one another. In particular, actuators that are laterally arranged alongside a limb, such as dampers or drives, result in a high construction volume, since the components cannot be arranged according to the body contour.

SUMMARY

The task of the present invention is to provide a joint device which can be easily adjusted to fit the respective user and requires as small a volume as possible.

According to the invention, this task is solved by a joint device featuring the properties disclosed herein. Advantageous configurations and embodiments of the invention are also disclosed in the description and the diagrams.

The joint device for a prosthesis or an orthosis, or of a prosthesis or an orthosis with an upper part, a lower part, with a joint that comprises a joint axis about which the upper part is mounted such that it can be swivelled relative to the lower part, and with an actuator that is designed to influence a swivelling of the upper part relative to the lower part, wherein the actuator is mounted at an upper part fixing point on the upper part and at a lower part fixing point on the lower part, provides for at least two joints that are arranged between the upper part fixing point and the lower part fixing point; for the joints to allow for a swivelling of the actuator relative to the upper part fixing point and the lower part fixing point, and for said joints to form at least one joint axis, at least one of which is not oriented parallel to the joint axis. The actuator need not be fixed directly to the upper part and the lower part; it may be mounted at the respective lower part fixing point or upper part fixing point via spacers, fixing components, extensions or further components. Due to the fact that at least two joints are arranged between the upper part fixing point and the lower part fixing point, it is possible that, even if the alignment of the upper part fixing point in relation to the lower part fixing point is not straight and the orientation of the actuator in relation to the joint axis is thus tilted or twisted, the actuator can still be fixed as close to the body or the upper or lower part as possible. This renders it possible to execute the articulation of the actuator and the mechanical structure, which absorbs the forces of the actuator and—in the case of an orthosis—transfers them to limbs, in such a way that an adjustment to fit the body contour is possible without any manual processing for the purpose of shaping the components. The same applies for prostheses, the mechanical structure of which generally consists of a socket as an upper part and a lower part that is fixed in an articulated manner to said upper part and the actuator of which transfers damping forces or propulsive forces to the upper part and lower. Given that, in general, orthotic components are provided as standard parts in different shapes and at different angles, they must be mechanically processed, for example deformed or shortened, so that they fit the contour of the respective limb, such as the leg. Similar conditions apply for prostheses, the sockets of which are often custom-made as unique products or, as test prosthetic sockets, can be individually adjusted to the body contour. In order to attach an actuator to the prosthesis or orthosis, mechanical post-processing is often required or it is necessary to provide spacers, so that the components that follow an extension or flexion movement are generally moved in one plane, which is perpendicular to the swivel axis. With the arrangement or configuration of at least two joints, which enable a swivelling of the actuator in relation to the upper part fixing point and the lower part fixing point and each form a swivel axis, at least one of which is oriented so as not to be parallel to the joint axis, it is possible to adjust the actuator to ensure an optimal fit to the body contour.

An embodiment of the invention proposes that the first swivel axis be oriented orthogonally to the joint axis, such that a tilting perpendicular to the joint axis is possible. This renders simple a tilting out of the plane that is perpendicular to the swivel axis.

An embodiment of the invention proposes that the first swivel axis be oriented orthogonally to the second swivel axis. An embodiment proposes that both swivel axes be oriented such that they are neither parallel to one another nor to the joint axis, meaning that the adjustability of the orientation of the actuator in relation to the joint axis and the respective fixing point can be almost arbitrary.

The two swivel axes preferably lie in the same plane and preferably intersect at a point. The point of intersection of the two swivel axes need not be a point on the joint axis; however, it is preferable if it does lie on the joint axis, so that all three axes intersect at a single point.

Preferably, the actuator is designed as a linear actuator and actively effects either a swivelling of the upper part relative to the lower part or dampens or brakes a swivel movement of the upper part relative to the lower part.

The actuator may be designed as an electric, pneumatic or hydraulic drive in the case of an active support of the respective movement, or as a hydraulic or pneumatic damper or as an electric, pneumatic, mechanical or magnetic brake if the actuator is to have a braking or damping effect.

An embodiment of the invention proposes that at least one of the swivel axes lie in a swivel plane that is oriented orthogonally to the joint axis. This may result in a twisting of the actuator about the swivel axis, without adversely affecting the movement about the joint axis.

An embodiment of the invention proposes that the actuator be fixed to a bracket, which is arranged between the joint axis and the upper part fixing point or the lower part fixing point. Here, at least one of the swivel axis is designed to be in the bracket. The bracket is therefore a spacer that is or can be attached to the lower part or the upper part. A part of the actuator is fixed to the bracket: for example, in the case of a linear actuator, said part may be the housing or the operating rod that moves in and out of the housing, such as a piston rod or a motor-driven extendible component. The respective other end of the actuator may then be fixed to the other component of the joint device, i.e. on the lower part or on the upper part, and forces of the actuator transferred to the respective component. Due to the configuration of a bracket for fixing between the actuator and the upper part or lower part, it is possible to provide a module that can be standardized and prefabricated, wherein said module is attached to the upper part or the lower part at the respective fixing point in order to create a coupling point or a bearing point with the actuator. As a result, cost-effective standard components can be used to render possible the adjustment of standard components to fit the individual body contour of the respective user.

The bracket may feature a mounting plate that is attached to the upper part or lower part such that it is torque-proof, in order to be able to effectively transfer forces and torques to the upper part or the lower part. Furthermore, the torque-proof attachment of the bracket to the upper part or the lower part enables a sufficiently stable guiding of the actuator on the upper part or lower part.

If the actuator is designed as a linear actuator, a bearing point is preferably provided on the bracket, said bearing point being situated at a distance from the joint axis, wherein the actuator is mounted on the bracket either with the housing or the extendible rod at said bearing point. This renders it possible to effect or withstand a torque about the joint axis, so as to effect or influence a swivelling of the upper part relative to the lower part.

In an embodiment of the invention, the actuator is attached to a frame, which features a fixing device or several fixing devices for the reversible arrangement on the upper part and the lower part. This frame allows for the production of a standardized interface, for example on a control system, sensors or other components that are fixed to said frame. The frame also allows for the production of an interface for the actuator, so that different upper parts or lower parts can be equipped in advance with fixing connectors for the fixing devices, such that different components can be tested on the frame. Such a configuration with a frame is practical for test orthoses or test prostheses in particular, since the respective components can be easily fixed to different upper parts, lower parts or also different components on the respective frame, such that a multitude of combinations would be possible without the need for mechanical changes to the upper parts, lower parts or components, or the use of a multitude of spacer elements.

One embodiment of the invention proposes that the bracket be fixed to the frame such that it can be swivelled and the joint axis and/or a swivel axis be configured between the frame and the bracket. The bracket and the frame thus form the actual joint between the upper part and the lower part, said joint transferring forces and torques. The combination of bracket and frame can be designed to be independent of the upper part and the lower part. The upper part or lower part of a prosthesis is, for instance, a prosthetic socket and a further prosthetic component, which is connected distally to said socket, such as a lower leg tube, a prosthetic foot or, in the case of upper limbs, a lower arm tube, whereas in the case of a prosthesis, the upper part and the lower part are designed in rails or fixing shells for attaching them to the respective limb or body part.

An embodiment of the invention proposes that, when the swivelling about the axis of movement occurs, the actuator conduct a movement in the plane that is defined by the frame. Here, the movement of the actuator is linked to the movement of the frame.

An embodiment of the invention proposes that at least one sensor be arranged on the joint device, the actuator, the frame and/or the bracket for recording angular positions, paths, forces, torques, spatial positions and/or accelerations, in order to control the activities of the actuator. To this end, the sensor is or the sensors are coupled with an electronic control device and, where applicable, with an interface for a user. The coupling may be wired or wireless. A wired or wireless interface for adjusting the control parameters of the actuator may be arranged in the interface for the user. An energy supply for providing the required electrical energy for the control system and the drive, or for the adjustment of valves, or for generating an electromagnetic field on the joint device, particularly on the frame, may also be provided.

BRIEF DESCRIPTION OF THE DRAWINGS

In the following, examples of embodiments of the invention will be explained in more detail by way of the attached figures. They show:

FIG. 2—a frontal view with a perpendicular alignment from upper part to lower part;

FIG. 3—a laterally tilted arrangement of the actuator;

FIG. 4—a medially tilted arrangement of the actuator;

FIGS. 6 to 8 depictions of a variation of the invention.

DETAILED DESCRIPTION

Figure 1:
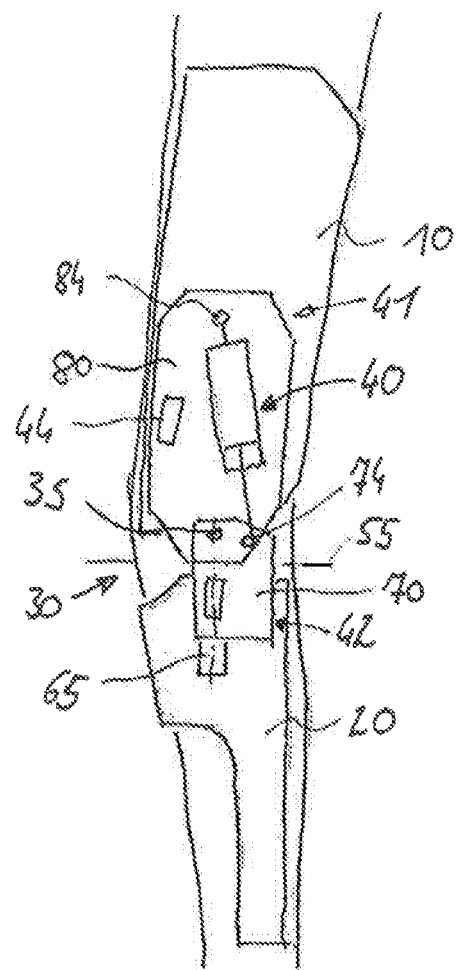
FIG. 1—a schematic lateral view of a joint device in the form of an orthosis.

FIG. 1 shows a lateral view of a joint device on an orthosis with an upper part 10, which is designed as a shell or a rail for attaching it to an upper leg. A lower part 20 is arranged to the upper part 10 about a joint axis 35, such that said upper part can be swivelled, wherein said lower part is also designed as a shell or as at least one rail. The upper part 10 and the lower part 20 are arranged on the respective limb via fixing elements, which are not depicted here. The example of an embodiment provides a knee orthosis, which is put on a leg of a user. The upper part 10 is thus designed as an upper leg shell or upper leg rail, where applicable as a combination of two rails that are arranged medially and laterally on the upper leg, whereas the lower part 20 is designed as a lower leg shell or lower leg rails.

The joint axis 35 is situated in the vicinity of the natural swivel axis of the respective joint; in the present example of an embodiment, this is the knee joint. Since the natural joint axis in a knee joint is variable, due to the complex structure of the knee joint, the joint axis 35 is situated in the vicinity of the natural joint axis or on a compromise pivot axis.

An actuator 40 is arranged between the upper part 10 and the lower part 20, wherein an extension movement or a flexion movement about the joint axis 35 can be influenced via said actuator. The actuator 40 may be designed as a passive actuator, in particular as a hydraulic damper, a pneumatic damper or a braking device, which is operated electrically, pneumatically, mechanically or magnetically. It is also possible to design the actuator 40 as a drive which operates electrically, pneumatically or hydraulically. Energy provision devices 44 are allocated to the respective drive, wherein such devices are used to supply the respective drive with the required energy. Said energy provision devices may be provided in the form of pressure accumulators, elastic elements or batteries or rechargeable batteries. Other energy stores are also possible and provided for. It is also possible for a drive 40 to also be used as a brake. In the example of an embodiment shown, the actuator 40 is designed as a linear actuator and features a housing, in which a piston or another force transmitter that can be operated linearly is arranged. In the case of a piston, it is connected to a piston rod, the end of which is mounted at a distal bearing point 74 on a bracket 70. The housing is arranged at an upper bearing point 84 on a frame 80. An upper fixing point 41 and a lower fixing point 42 are configured by way of the frame 80 and the bracket 70, so that the actuator 40 is mounted at an upper part fixing point 41 and a lower part fixing point 42 on the upper part 10 and the lower part 20 via the frame 80 and the bracket 70. It is also possible for the upper bearing point 84 to be provided directly on the upper part 10. A reverse arrangement of frame and bracket is also possible, or the attachment of the actuator 40 with the housing to the bracket 70 on the lower part 20.

In the example of an embodiment shown, the joint 30 is configured by way of the frame 80 and the bracket 70. Two joints are arranged inside the bracket 70 and between the bearing point 74 on the bracket 70 and the lower part fixing point 42, wherein only the swivel axes 55, 65 of said joints are depicted due to the schematic depiction. The bracket 70 and thus also the actuator 40 can swivel about the swivel axes 55, 65 relative to the lower part 20, wherein the swivel range about the swivel axes 55, 65 is restricted by end stops. In the example of an embodiment shown, all three axes—the joint axis 35 and the swivel axes 55, 65—are perpendicular to each other. However, this need not necessarily be the case. Preferably, all three axes 35, 55, 65 intersect at a point so as to enable the execution of the medial and lateral swivelling as well as a rotation about the longitudinal direction of the lower part 20 or the limb, without adversely affecting the swivel movement about the joint axis 35.

FIG. 2 shows a frontal view of the embodiment according to FIG. 1. In FIG. 2, the upper part fixing point 41 and the lower part fixing point 42 can be seen more clearly. The joint axis 35 generally extends horizontally through the natural joint. On the side that lies opposite to the actuator 40, the orthosis features a free motion joint 12 to allow the upper part 10 to be guided more effectively relative to the lower part 20. FIG. 2 also depicts fixing agents 25 in the form of a belt, by way of which the lower part 20 can be attached to the lower leg. Corresponding fixing agents are provided on the upper part 10. In the configuration according to FIG. 2, the leg is straight, the upper part 10 and the lower part 20 are correspondingly aligned with one another such that they are straight, the respective longitudinal direction from upper part 10 to lower part 20 runs in a common plane or in planes that are parallel or generally parallel to one another. The outer surfaces of the upper part 10 and of the lower part 20 generally lie in a plane perpendicular to the joint axis 35, such that both the actuator 40 as well as the frame 30 and the bracket 70 can be fixed so that they fit very closely to the body or the upper part 10 and the lower part 20. An ability to twist or swivel about one of the swivel axes 55, 65 is not necessary, or is only necessary to a low degree, to compensate for misalignments.

FIG. 3 depicts a possible variation of an upper part configuration. The upper part 10 protrudes laterally beyond a swivel plane 350, which is oriented perpendicular to the joint axis 35; the actuator 40 with the frame 80 is tilted out of the swivel plane 350 by approximately 35 degrees. To compensate for this tilting, a joint is provided in the bracket 70, said joint enabling a swivelling about the swivel axis 55. The swivelling of the actuator 40 out of the swivel plane 350 causes, upon actuation, a torque, which effects a swivelling about the perpendicular swivel axis 65. Due to the design of a joint 60 that can be twisted about the swivel axis, a rotation of the actuator 40 can be prevented if the joint 30 is inflected or extended.

A corresponding configuration is shown in FIG. 4, in which a medial deflection of the actuator 40 takes place, rather than a lateral deflection.

FIGS. 2 to 4 depict various free motion joints 12: FIG. 2 shows a ball joint, FIG. 3 a hinge joint and FIG. 4 a cardan joint.

Figure 5:
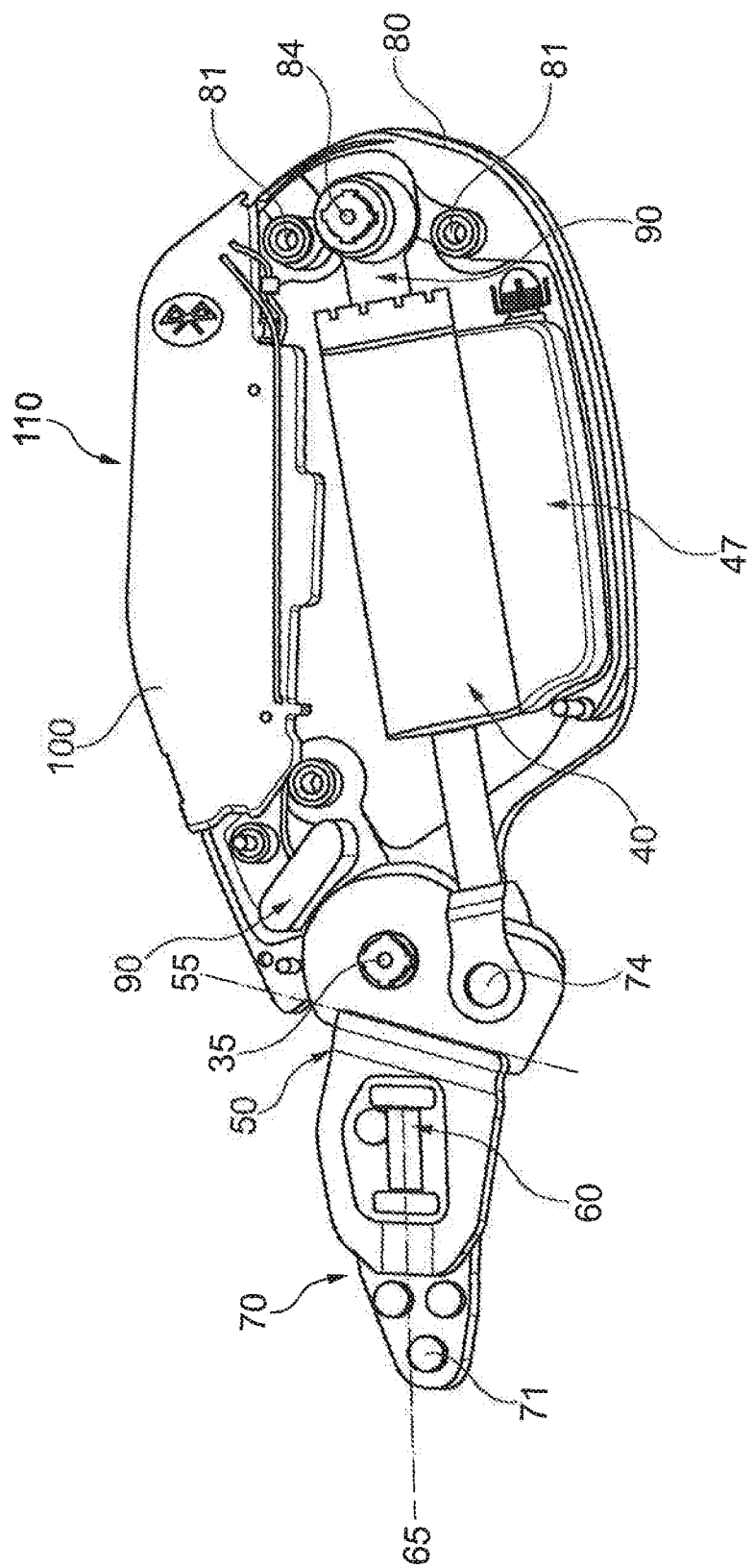
FIG. 5—a top view of a joint device in the form of a frame, which is flexibly connected to a bracket.

FIG. 5 depicts a detailed view of the actuator 40 as a linear actuator in the form of a hydraulic damper with a valve unit 47, which can be controlled via an electronic control system 100. The electronic control system 100 is coupled with sensors 90, which record forces and angular positions in the example of the embodiment shown. An angle sensor 90 is depicted close to the joint axis 35; it also shows a force sensor 90 at an upper bearing point 84 of the actuator 40. The bearing point 84 is designed on a frame 80, on which both the actuator 40 and the control unit 100 are arranged, as well as a user interface 110. An additional sensor device may be arranged on the control unit 100, said sensor device recording the spatial position. A so-called spatial position sensor delivers data on the position of the frame 80 or the actuator 40 in the space; in particular, data is delivered on the orientation relative to the direction of gravity.

Several fixing devices 81 in the form of pins or through-bores are provided on the frame 80, which may be designed to be made from, for example, a dimensionally stable plastic, where applicable a fiber-reinforced or a metal; said fixing devices can be used to reversibly attach the frame 80 to the upper part 10, not depicted. Further components, especially energy stores, may also be arranged on the frame 80. Various bearing points 84 may be prepared on the frame 80, so as to enable the simple attachment of different actuators or components to the frame 80.

A bracket 70 is arranged about the joint axis 35 on the frame 80 such that it can be swivelled, wherein said bracket forms the joint device with the frame 80. The bracket 70 is attached to the lower part 20, not depicted, via fixing devices 71 on a mounting plate 70a, wherein the attachment is preferably torque-proof. The fixing devices 71 may be designed as rivets or screws or similar fixing elements, said fixing elements preferably working in a form-fitting manner. Via the fixing devices 71, the bracket 70 can be reversibly attached, via the mounting plate 70a, to a lower part 20.

Two joints 50, 60 are designed to be situated in the bracket 70, said joints enabling a swivelling of the bearing point 74 relative to the mounting plate 70a. A first joint 50 enables a swivelling about a first swivel axis 55. The first swivel axis 55 lies in a plane orthogonal to the joint axis 35 and enables a tilting in an approximately mediallateral direction if the frame 80 and the bracket 70 are arranged laterally on the outer side of an orthosis. The second swivel axis 65, which is formed by the second joint 60, lies in the same plane. The swivel axis 65 generally extends in the longitudinal direction of the joint device and preferably passes through the joint axis 35. It is also preferable if the first swivel axis 55 passes through the joint axis 35. Both swivel axes 55, 65 may, but do not have to, stand at a right angle to one another; in the example of an embodiment shown, the two swivel axes 55, 65 are not perpendicular to one another. The joints 50, 60 are configured on the bracket 70, which is connected to the mounting plate 70a such that it can be twisted. This mounting plate is part of the bracket 70 and connected to the lower part 20 such that it is torque-proof.

A distal bearing point 74 is also configured on the bracket 70 at a distance from the joint axis 35, wherein said bearing point is provided for mounting of the piston rod on the bracket 70. The bearing point 74 enables a swivelling about an axis, said swivelling being generally parallel to the joint axis 35.

The fixing of the actuator 40 to the upper part 10 and the lower part 20 occurs on the one hand via the frame 80 and via the bracket 70 on the other. Via their respective fixing devices 71, 81, the frame 80 and the mounting plate 70a form the upper part fixing point 41 and the lower part fixing point 42. The linear actuator 40 is attached to the frame 80 via the bearing point 84 such that it can be twisted. The mounting plate 70a and the frame 80 are also attached to the lower part 20 or the upper part 10 such that they are torque-proof, so that the piston rod moves in and out of the housing of the linear actuator 40 upon a swivelling about the joint axis 35.

With regards to FIGS. 2 to 4, it becomes clear that above all in the field of orthotics, but also in prosthetics, the situation may arise in which the components used should be mounted as closely as possible to the preserved body parts, so as to ensure that an additional volume on the body is kept as small as possible. Via the actuator 40, it is possible to achieve a targeted support of a torque in the flexion and extension direction at different phases of the movement, for example when walking, whenever a support or guide is required. To this end, the actuator 40 is articulated on the joint device in such a way that the linear movement of the actuator effects a torque that either supports or resists the movement. Whereas in the past it was necessary to guarantee, via spacers, that the actuator 40 was always positioned in the swivel plane 350, the joint device according to the invention renders it possible for the articulation of the actuator 40 and the remaining mechanical structure, which serves to transfer loads, to be adjusted to fit the body contour or the respective different configurations of the orthosis or prosthesis, without requiring any manual processing, such as deformation or the arrangement of spacers. Here, the movement of the linear actuator 40 occurs in a plane that is different from the swivel plane 350, which is oriented perpendicular to the joint axis 35. The arrangement in a single plane renders it possible to keep the construction volume that is required low. Such joint devices allow for the construction of compact, mechatronic orthoses or prostheses. In the field of prosthetics, they can be used, for instance, for patients who have a very long stump or for small patients. By way of a lateral mounting of a joint device according to the invention, a simple prosthetic joint with a hinge joint can be rendered more functional. The same applies for ankle joint or hip prostheses, and generally also for upper limb prostheses. The joint device, especially in the case of a modular configuration with a frame 80 and a mounting plate 70a, enables the simple production of test prostheses or test orthoses. Furthermore, different actuators, such as dampers or drives, can be easily attached to preferred standardized fixing points on the upper part and the lower part, such that a wide variety of components can be tested on the respective patient.

With the joint device according to the invention, the positioning of the actuator 40 and the mechanical structure used for transferring a load, in the form of the upper part and the lower part, can be varied in its angular alignment in all three spatial directions, particularly in the frontal plane about an anterior-posterior axis, without requiring any manual adjustments or spacer elements. When the optimal angular position of the actuator in relation to the body contour of the user is found, this optimal angular position can be fixed by way of an external free motion joint 12. The free motion joint 12 is arranged on the contralateral side, in particular on the medial side, since the actuator unit is generally arranged laterally on a patient. The rotational axis of an orthosis, such as the joint axis 35, is preferably realized by two points: one being on the joint device 30, on the side of the actuator 40, and the other being on a free motion joint 12, on the contralateral side.

The configuration according to the invention allows the actuator to move on a path that deviates from the swivel plane 350, which is defined by a plane that is perpendicular to the compromise pivot axis of the joint. The additional joints 50, 60 prevent a rotation of the actuator 40 and minimize the volume covered during the movement, meaning that the construction volume required is lower than the construction volume of configurations known to date. The alignment of the mechanical components on the upper part 10 and the lower part 20 is defined over the course of the mounting of an orthosis or prosthesis. In the case of an orthosis, the orthosis is stabilized via the mechanical free motion joint 12 and sufficiently defined in its degrees of freedom.

Figure 6:
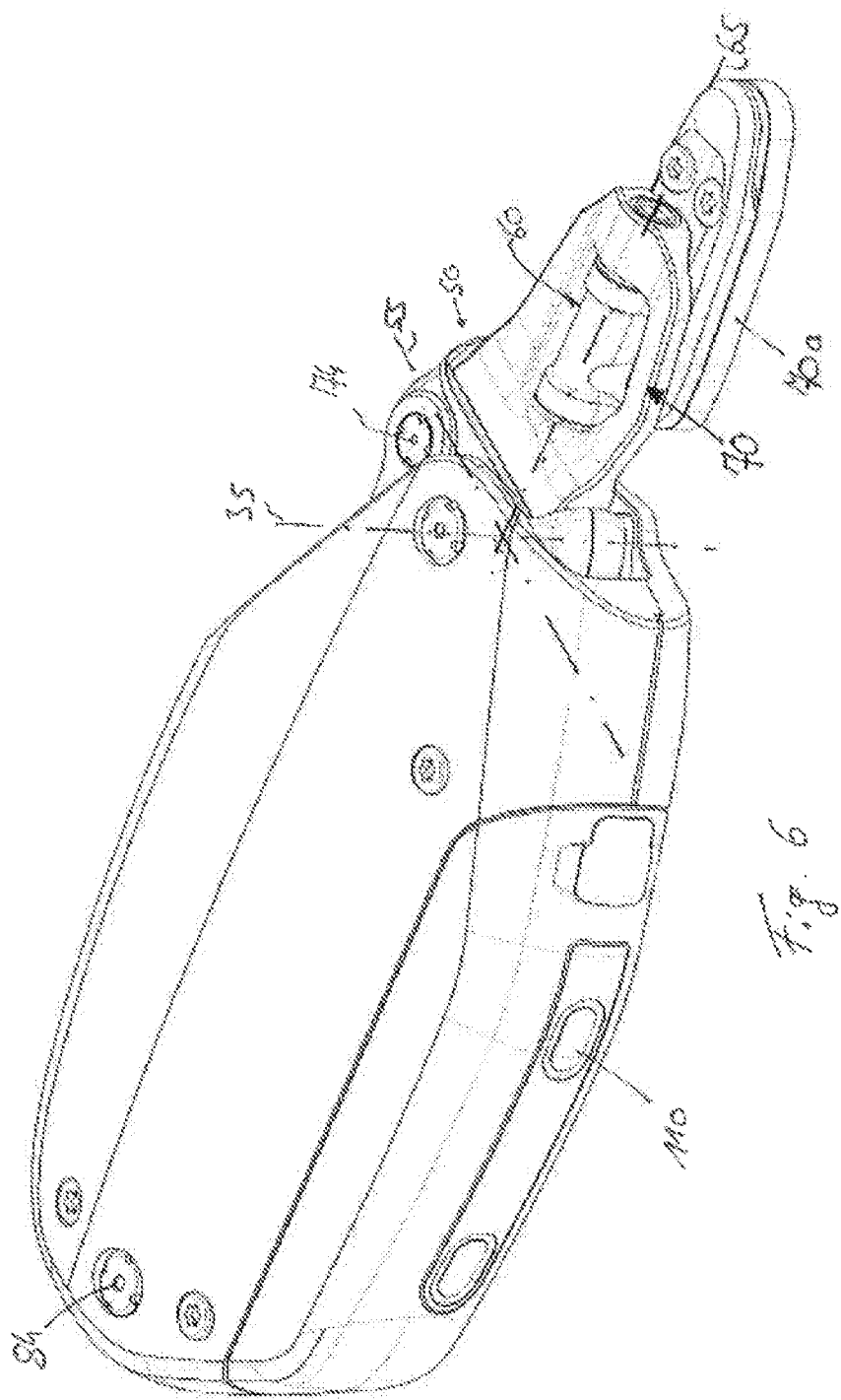
Figure 7:
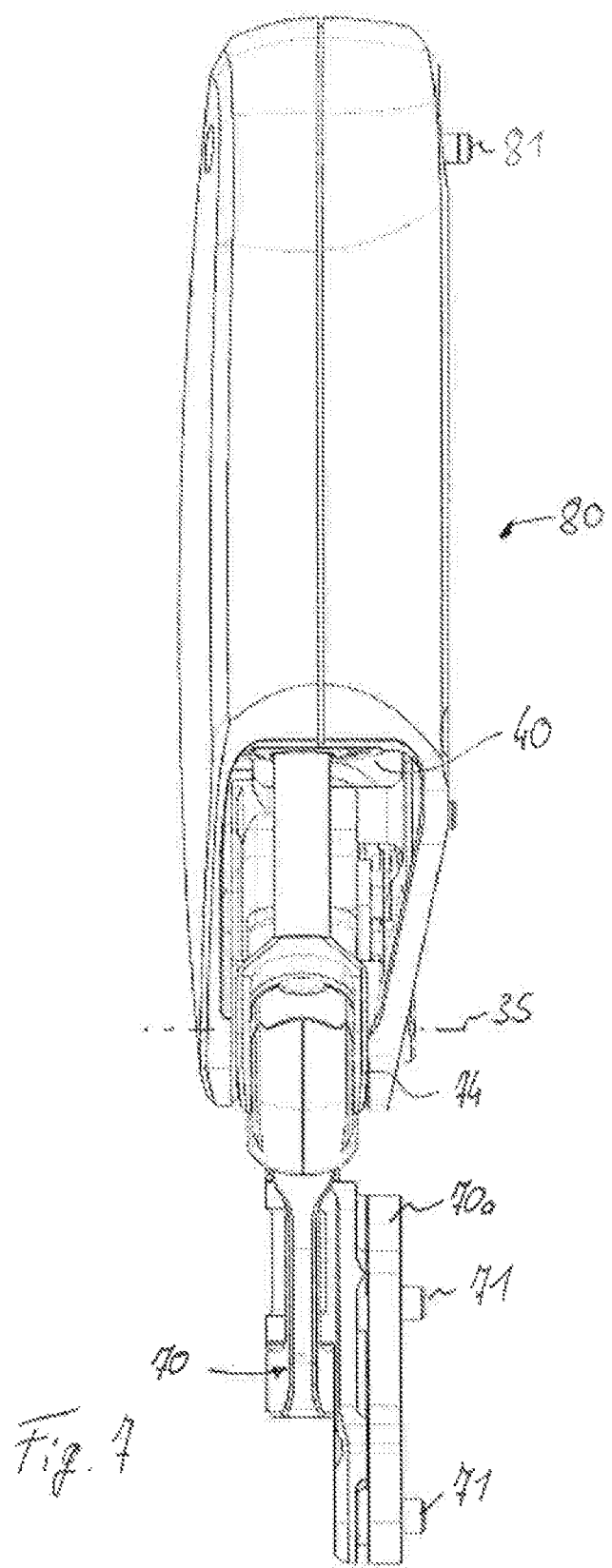

FIGS. 6 to 8 depict another variation of the invention, in which the actuator 40 is concealed on the frame 80 behind a cladding. As can be seen in FIG. 6, the interface 110 is accessible from outside, wherein said interface is an interface between the control unit 100 that is fixed to the frame and the user or an external computer device. The upper, proximal bearing point 84 can be seen, as can the lower, distal bearing point 74. The bracket 70 comprises two joints 50, 60, wherein the swivel axes 55, 65 of the two joints 50, 60 are situated in the swivel plane 350, orthogonal to the joint axis 35. The joint axis 35 is formed by a cardan joint-like connection between the bracket 70 and the frame 80, and attached via the free motion joint 12. Both swivel axis 55, 65 intersect on the joint axis 35.

FIG. 7 shows a rear view of the joint device with the frame 80 and the bracket 70 and the respective lateral fixing devices 71, 81, such as bolts or screw receptacles, said fixing devices protruding in the medial direction. The joint axis 35 can be recognized, as can the linear actuator 40 inside the housing on the frame 80 and the distal bearing point 74.

FIG. 8 shows a lateral view, in which the frame 80 is viewed from the medial direction, i.e. from the direction of the orthosis. The joint axis 35 extends orthogonally out of the sheet plane; correspondingly, the sheet plane forms the swivel plane 350. The distal bearing point 74 of the linear actuator is arranged at a distance from the joint axis 35, so as to be able to build up a torque about the joint axis 35 or absorb forces. A total of three fixing devices 81 are configured on the side of the frame 80 that faces the orthosis; by way of said fixing devices, the frame 80 can be fixed to the upper part such that it is stable and torque-proof. Two fixing devices 71 are arranged on the mounting plate 70a, by means of which the mounting plate 70a can be attached to the lower part, not depicted, such that it is torque-proof and stable with regards to its position. The fixing devices 71, 81 allow for a reversible fixing of the joint device, which in this case is formed via the frame 80 and the bracket 70.

Unlike an arrangement via a frame 80, the actuator can also be fixed directly to an upper part or a lower part.

We claim:

1. A joint device of an orthosis or prosthesis or for an orthosis or prosthesis comprising:
    an upper part;
    a lower part;
    a joint that comprises a joint axis, about which the upper part is mounted such that the upper part can be swiveled relative to the lower part;
    an actuator, which is designed to swivel the upper part relative to the lower part, the actuator is mounted at an upper part fixing point on the upper part and at a lower part fixing point on the lower part; and
    at least two joints arranged between the upper part fixing point and the lower part fixing point, the at least two joints enable a swiveling of the actuator relative to the upper part fixing point and the lower part fixing point, and the at least two joints each form at least one swivel axis, at least one of which is not oriented parallel to the joint axis,
    wherein the actuator is fixed to a bracket, which is arranged between the joint axis and the upper part fixing point or the lower part fixing point, wherein each swivel axis formed by the at least two joints and the joint axis each extends through the bracket, and wherein the swivel axes lie in a common plane.

2. The joint device according to claim 1, wherein the swivel axes include a first swivel axis that is oriented orthogonally to the joint axis.

3. The joint device according to claim 1, wherein a first of the swivel axes is oriented orthogonally to a second of the swivel axes.

4. The joint device according to claim 1, wherein the swivel axes are oriented neither parallel to each another nor to the joint axis.

5. The joint device according to claim 1, wherein the actuator is designed as a linear actuator.

6. The joint device according to claim 1, wherein the actuator is designed as an electrical, pneumatic or hydraulic drive, or a hydraulic or pneumatic damper, or an electrical, pneumatic, mechanical or magnetic brake.

7. The joint device according to claim 1, wherein the swivel axes and the joint axis intersect at a common point.

8. The joint device according to claim 1, wherein at least one of the swivel axes lies in a swivel plane, which is oriented perpendicular to the joint axis.

9. The joint device according to claim 1, wherein the bracket comprises a mounting plate, which is attached to the upper part or the lower part such that the mounting plate is torque-proof.

10. The joint device according to claim 1, wherein the joint axis is configured between the upper part and the bracket or between the lower part and the bracket.

11. The joint device according to claim 1, wherein the actuator is designed as a linear actuator and is mounted on the bracket at a bearing point at a distance from the joint axis.

12. The joint device according to claim 1, wherein the actuator is attached to a frame, which comprises fixing devices for the reversible arrangement on the upper part or the lower part.

13. The joint device according to claim 12, wherein the bracket is fixed to the frame such that the bracket can be swiveled and at least one of the joint axis and the swivel axis is configured between the frame and the bracket.

14. The joint device according to claim 12, wherein, when the swiveling about the joint axis occurs, the actuator conducts a movement in a plane that is defined by the frame.

15. The joint device according to claim 12, wherein at least one sensor is arranged for recording at least one of angular positions, paths, forces, torques, spatial positions and accelerations on at least one of the joint device, the actuator, the frame and the bracket.

16. A joint device of an orthosis or prosthesis or for an orthosis or prosthesis comprising:
    an upper part;
    a lower part;
    a joint pivotally coupling the upper and lower parts together about a joint axis;
    an actuator operable to pivot the upper part relative to the lower part, the actuator being mounted at an upper part fixing point on the upper part and at a lower part fixing point on the lower part; and
    at least two actuator joints arranged between the upper part fixing point and the lower part fixing point, the at least two actuator joints permitting pivoting of the actuator relative to the upper part fixing point and the lower part fixing point, and the at least two actuator joints each form at least one actuator pivot axis, at least one of which is not oriented parallel to the joint axis,
    wherein the actuator is fixed to a bracket, which is arranged between the joint axis and the upper part fixing point or the lower part fixing point, wherein each pivot axis formed by the at least two joints and the joint axis each extends through the bracket, and wherein the pivot axes lie in a common plane.

17. The joint device according to claim 16, wherein the actuator pivot axes include a first pivot axis that is oriented orthogonally to the joint axis.

18. The joint device according to claim 16, wherein a first of the actuator pivot axes is oriented orthogonally to a second of the actuator pivot axes.

* * * * *